United States Patent [19]

Grüning et al.

[11] Patent Number: 5,645,842
[45] Date of Patent: Jul. 8, 1997

[54] COSMETIC OR PHARMACEUTICAL PREPARATIONS

[75] Inventors: Burghard Grüning; Christian Weitemeyer, both of Essen, Germany

[73] Assignee: Th. Goldschmidt AG., Essen, Germany

[21] Appl. No.: 684,797

[22] Filed: Jul. 18, 1996

Related U.S. Application Data

[63] Continuation of Ser. No. 138,299, Oct. 18, 1993, abandoned.

[30] Foreign Application Priority Data

Oct. 31, 1992 [DE] Germany ............ 42 36 861.8

[51] Int. Cl.$^6$ ..................... A61K 7/48
[52] U.S. Cl. .............. 424/401; 424/59; 424/78.01; 514/844; 514/846; 514/937; 514/938; 514/939
[58] Field of Search ............ 424/401, 59, 78.01; 514/844, 846, 937, 938, 939

[56] References Cited

U.S. PATENT DOCUMENTS 4,824,983  4/1989  Fink et al. ............... 556/454

FOREIGN PATENT DOCUMENTS 0211550  7/1986  European Pat. Off. .

OTHER PUBLICATIONS

D. Schaefer, Silicone Surfactants, 1990, total of 6 pgs.

*Primary Examiner*—Jyothsna Venkat
*Attorney, Agent, or Firm*—Anderson Kill & Olick P.C.

[57] ABSTRACT

Cosmetic or pharmaceutical preparations, which contain natural or synthetic oils having ester groups or mineral oils, are characterized by containing a selected organopolysiloxanes with long-chain alkyl or alkoxy groups for improving the spreading behavior of the oils, particularly on the human skin. The organopolysiloxanes are added to the oil in amounts of 0.003 to 20% by weight, based on the total weight of oil and organopolysiloxane.

4 Claims, No Drawings

COSMETIC OR PHARMACEUTICAL PREPARATIONS

This is a continuation of application Ser. No. 08/138,299, filed Oct. 18, 1993, abandoned.

FIELD OF INVENTION

The invention relates to cosmetic or pharmaceutical preparations containing natural or synthetic oils having ester groups or mineral oils and exhibiting improved spreading behavior.

BACKGROUND INFORMATION AND PRIOR ART

It is well known that polysiloxanes improve the spreading of oils on the surfaces of, for example, human skin, but also on the surfaces of plastics. Reference is made to the European publication 0 211 550 with regard to this state of the art. This relates to a composition, which contains the following:

(A) 5 to 95% by weight of an alkoxylated polyether having the formula

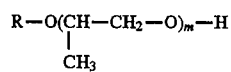

wherein R represents a saturated or unsaturated $C_{6-22}$ hydrocarbon group, which can be substituted by a hydroxyl group, and m represents 2 to 50, and (B) 95 to 5% by weight of tetra(dimethylcyclosiloxane) or penta(dimethylcyclosiloxane) or a mixture thereof.

Polyethers, containing such silicone oils, can be used in the form of creams or lotions. They can also, however, be used as carriers for physiologically active substances, including pharmaceutical substances. The main property of such a preparation consists in its improved ability to spread on skin. The spreadability depends, among other things and in particular, on the surface tension of the preparation containing the silicone, reference being made in the European publication 0 211 550 to the paper by R. Keymer: "The Spreading of Liquid Lipoids on Skin", Pharm. Ind. 32 (7), 577–581 (1970).

Silicone waxes represent a further class of spreading agents, which have one or more long-chain alkyl groups linked to the silicone backbone. The melting point of the silicone waxes increases as the content of long-chain alkyl groups increases and as the chain length of the alkyl group increases. In this connection, reference is made to the paper "Silicone Surfactants", D. Schaefer, Tenside 1990, pages 154 to 158. These silicone waxes lower the surface tension of organic systems, such as the surface tension of mineral oils, and improve the spreading ability of cosmetic oils and waxes. As a rule, however, the spreading ability of mixtures of oils and silicone waxes is only slightly better than that of pure oils.

A disadvantage of the polysiloxanes, used as agents for improving the spreading ability, is their generally poor compatibility with oils, the compatibility (solubility) of the polysiloxanes with the oils decreases as the number of dimethylsiloxy units increases.

The invention is concerned with the technical problem of finding organopolysiloxanes, which have as good a compatibility with (solubility in) organic oils as possible and have the ability to improve the spreadability of the oils on surfaces, particularly on the human skin. The compounds are to be clearly effective in the least possible amounts and should be in a position to improve the spreading behavior even of oils of different structures.

OBJECT OF THE INVENTION

An object of the present invention is cosmetic or pharmaceutical preparation comprising organopolysiloxanes and natural or synthetic oils having ester groups or mineral oils and exhibiting an improved spreading behavior. Another object of the invention is the above preparation wherein the organopolysiloxanes are selected according to the molecular weight of the oils. In yet another object of the invention directed to the above preparation, organopolysiloxanes are selected depending on the viscosity of the oils.

The main preparation is characterized by containing organopolysiloxanes of the general formula

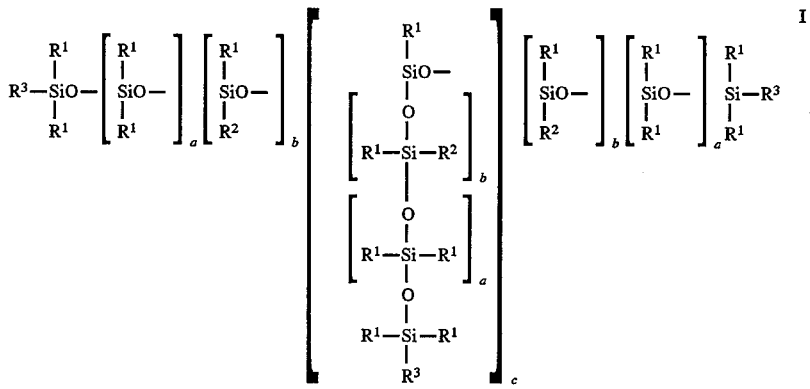

wherein the groups $R^1$ in the polymer are the same or different and represent alkyl groups with 1 to 4 carbon atoms, with the proviso that at least 90% of the $R^1$ groups are methyl groups, $R^2$ in the polymer are the same or different and (1) can be linear or branched alkyl groups with 8 to 30 carbon atoms, wherein the alkyl groups can be interrupted by an oxygen atom, or (2) can be linear or branched alkoxy groups with 8 to 30 carbon atoms, wherein the alkyl group of the alkoxy groups can be interrupted by an oxygen atom, $R^3$ represents the $R^1$ or the $R^2$ group, a has a value of 5 to 100, b has a value of 0 to 80, and c has a value of 0 to 5, with the proviso that (i) in the average molecule, at least two $R^2$ groups are as defined in (1) and/or (2) above, (ii) a>b and the sum of the units with the subscript a>10, and (iii) the organopolysiloxane is homogeneously miscible with the oil in a concentration of 0.01 to 20% by weight, in amounts of 0.003 to 20% by weight based on the total weight of oil and organopolysiloxane.

In Formula I, the $R^1$ groups in the polymers can be the same or different. They are alkyl groups with 1 to 4 carbon atoms and can be linear or branched. Examples of such groups are methyl, ethyl, propyl, isopropyl, butyl or isobutyl groups.

At least 90% of the $R^1$ groups must be methyl groups, the 90% being calculated on a numerical basis. Preferably, all $R^1$ groups are methyl groups.

The $R^2$ groups are groups with which the organopolysiloxanes are modified and which bring about the compatibility with oils.

The $R^2$ can be the same or different in the polymer and have the following meanings:

(1) linear or branched alkyl groups with 8 to 30 carbon atoms, wherein the alkyl groups can be interrupted by an oxygen atom, or (2) linear or branched alkoxy groups with 8 to 30 carbon atoms, wherein the alkyl group of the alkoxy groups can be interrupted by an oxygen atom.

At the same time, however, the condition must be fulfilled that, in an average molecule, at least two $R^2$ groups have the meaning given in (1) and/or (2).

As linear or branched alkyl groups (2) with 8 to 30 carbon atoms, 2-ethylhexyl, octyl, isononyl, decyl, undecyl, 2-butyloctyl, dodecyl, behenyl and 2-decyltetradecyl groups as well as the corresponding alkoxy groups, for example, are utilized. Preferred groups are the dodecyl, isotridecyl, 2-hexadecyl, hexadecyl, octadecyl and 2-decyltetradecyl groups as well as the corresponding alkoxy groups.

The concept of "alkyl groups, which can be interrupted by an oxygen atom", is understood to comprise, within the scope of this invention, groups of the type —R'—O—R", wherein R' is a divalent aliphatic group and R" a univalent aliphatic group. Such a group is, for example, the —(CH$_2$)$_3$—OC$_{12}$H$_{15}$ group. Further examples are the isotridecyloxypropyl, hexadecyloxypropyl, octadecyloxyhexyl and dodecyloxyundecyl groups.

The same is true for the concept "alkoxy group, the alkyl group of which can be interrupted by an oxygen atom". This definition is to include groups of the general formula —O—R'—O—R", in which R' and R" are defined as above. An example is the —O—(CH$_2$)$_2$—O—C$_{12}$H$_{15}$ group.

The $R^2$ groups are generally introduced into the organopolysiloxane molecule by reacting the appropriate hydrogen-siloxanes with olefins or unsaturated ethers in a hydrosilylation reaction, the double bond of the olefins being terminal and the number of carbon atoms of the olefins corresponding to the desired $R^2$ group.

The alkyl groups or the alkyl groups interrupted by an oxygen atom can, however, also be linked over an oxygen atom to the silicon atom of the polysiloxane backbone. These alkoxy groups can be introduced into the molecule of the polysiloxane by reaction with an SiH group or an SiCl group.

The subscript a refers to the number of dialkylsiloxy units and has a value of 5 to 100. Since at least 90% of the $R^1$ groups must be methyl groups, the dialkylsiloxy units must therefore be predominantly dimethylsiloxy units. The sum of the units with the subscript a must be greater than 10. This means that, when a=5, c cannot assume the value of 0.

Subscript b indicates the number of difunctional siloxy units which have the $R^2$ group. Subscript b has a value of 0 to 80. Since, however, the condition applies that at least two $R^2$ groups in the average molecule must have the meaning defined under (1) or (2), the two terminal $R^3$ groups must have the meaning of $R^2$ groups when b=0.

Subscript C indicates the number of branched, trifunctional siloxy units and has a value of 0 to 5. If c is equal to 0, b preferably has a value of 0 to 20.

$R^3$ can assume the meanings of the $R^1$ or $R^2$ group. When subscript b is equal to 0, $R^3$ must have the meaning of the $R^2$ group.

The organopolysiloxanes, contained in the inventive preparation, must fulfill a further condition, namely, they must be miscible with the oil contained in the inventive preparation at a concentration of 0.01 to 20% by weight, based on the total weight of oil and organopolysiloxane. It can be expected of any expert to select an inventive organopolysiloxane, which fulfills the miscibility condition, by varying the chain length of the $R^2$ group with the meaning given in (1) and (2) and by selecting different values for the subscripts a and b.

It has been observed that the spreading capability of natural or synthetic oils containing ester groups is improved by organopolysiloxane, which are selected according to the molecular weight of the oils. Another object of the invention, therefore, is the inventive preparation that comprises, as oils, natural or synthetic oils having ester groups and organopolysiloxanes that are selected according to the molecular weight of the oils, wherein, for oils of a molecular weight i) >500 the sum of the units with the subscript a=12 to 35, the sum of the units with the subscript b=3 to 10, and the subscript c=0, ii) >400 and <500 the sum of the units with the subscript a =25 to 60, the sum of the units with the subscript b=5 to 15 and the subscript c=0, iii) <400 the sum of the units with the subscript a=45 to 100, the sum of the units with the subscript b=3 to 20 and the subscript c=0.

These selection rules show that, as the molecular weight of the oil decreases, the number of units with the subscripts a and b increases.

A similar selection is possible for the oils based on mineral oils, for which, instead of the molecular weight, the viscosity is selected as the dimensioning parameter.

Another object of the invention is the inventive preparation that comprises mineral oil as oils and organopolysiloxanes that are selected depending on the viscosity of the oils, for oils having a viscosity at 25° C. of (i) >50 mpas the sum of the units with the subscript a=12 to 60, the sum of the units with the subscript b=3 to 15, and the subscript c=0, (ii) <50 mpas the sum of the units with the subscript a=26 to 100, the sum of the units with the subscript b=3 to 20, and the subscript c=0,

SUMMARY OF THE INVENTION

In the following, organopolysiloxanes of the general Formula I are shown. In addition, the oils, for the improvement in the spreading of which the particular compounds are particularly suitable, are indicated.

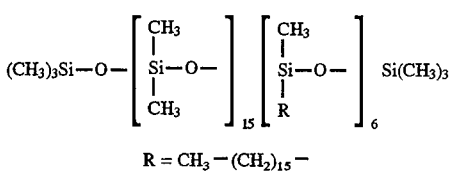

for ester oils with molecular weights in excess of 500 and for mineral oils with viscosities greater than 50 mpas (25° C.).

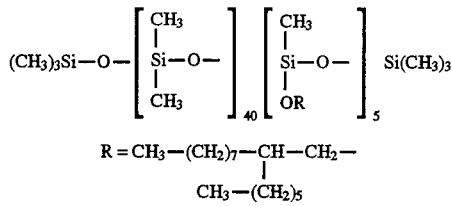

for ester oils with molecular weights of 400 to 500 and for mineral oils with viscosities greater than 50 mpas (25° C.).

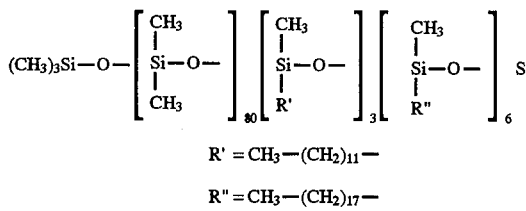

for ester oils with molecular weights less than 400 and for mineral oils with viscosities less than 50 mpas (25° C.).

Suitable as oils on the basis of natural or synthetic oils containing ester groups, are the oils known from the state of the art, which are liquid or become liquid during the application, such as ester oils, animal oils, vegetable oils and fats.

Examples of ester oils are decyl oleate, diethylhexyl adipate and pentaerythritol tetraethyl hexanoate. As animal or vegetable oils and fats, the esters of glycerin with most of the natural occurring fatty acids are suitable. An example of these is avocado oil. However, total or partial esters of higher functional alcohols, such as sorbitol, also come into consideration. A further example of useable oils is jojoba oil.

Examples of suitable mineral oils are branched hydrocarbon oils, paraffin oils of different viscosity, low-melting waxes and, in a further sense, squalene and squalane.

The oils, which are contained in the inventive preparations and contain the selected organopolysiloxanes of Formula I, exhibit outstanding spreading behavior already at very low contents of organopolysiloxanes. These organopolysiloxanes are added to the oils in amounts of 0.003 to 20% by weight, based on the total weight of oil and organopolysiloxane, a content of 0.01 to 5% by weight and, especially, a content of 0.1 to 2% by weight being particularly preferred.

The inventive cosmetic or pharmaceutical preparations can be used in the form of oils containing the selected organopolysiloxanes or in the form of solutions or emulsions. The emulsions can be cream or lotion and can be present in the form of an O/W or W/O emulsion. It is also possible to use these oils as carrier substances for active ingredients. Examples of active ingredients are pigments, fragrances, cosmetically and/or pharmaceutically active substances, such as vitamin E or esters of nicotinic acid.

Oils, which contain organopolysiloxane of Formula I, are particularly suitable for the preparation of highly effective sunscreens.

The object of the invention is explained in greater detail in the following examples, it being understood that the Examples are provided by way of illustration and not by way of limitation. The effect of the organopolysiloxanes, which are to be used pursuant to the invention, on the spreading capability of oils, is shown in Example 1 and the composition, preparation and properties of 10 cosmetic emulsions is shown in Examples 2 to 6.

In examples 2 to 6, the formulations are arranged in pairs. Each pair is labeled I or II. The difference consists in each case in the use of an oil phase with improved spreading capability in Formulation II, which otherwise is identical with Formulation I. Formulations II represent inventive formulations, while Formulations I are given for comparison.

EXAMPLE 1

The average formulas of the alkylsiloxanes used are listed in the following and are referred to in an abbreviated fashion as A to G. The solutions with the alkylsiloxanes A and B are not of the invention and are used only for comparison purposes. The solutions with the alkylsiloxanes C to G are of the invention.

Alkylsiloxane of formula A, not of the invention, comparison substance:

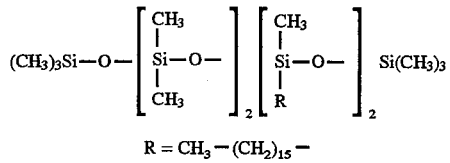

Alkylsiloxane of formula B, not of the invention, comparison substance:

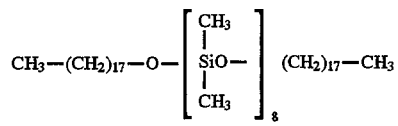

Alkylsiloxane of formula C, of the invention:

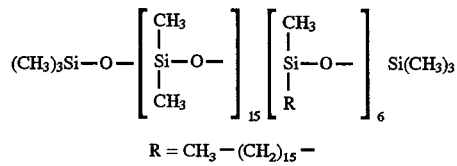

Alkylsiloxane of formula D, of the invention:

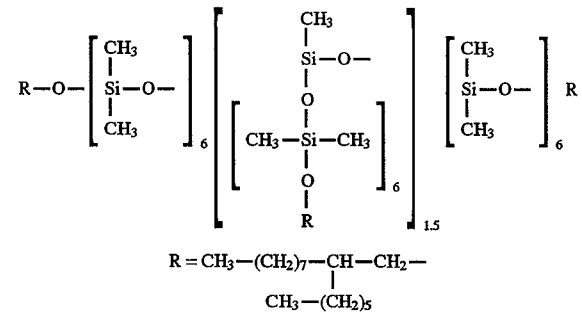

Alkylsiloxane of formula E, of the invention:

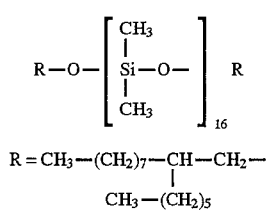

$R = CH_3-(CH_2)_7-CH-CH_2-$
        $|$
        $CH_3-(CH_2)_5$

Alkylsiloxane of formula F, of the invention:

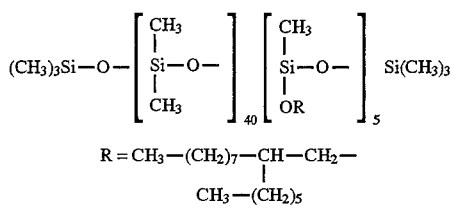

$R = CH_3-(CH_2)_7-CH-CH_2-$
        $|$
        $CH_3-(CH_2)_5$

Alkylsiloxane of formula G, of the invention:

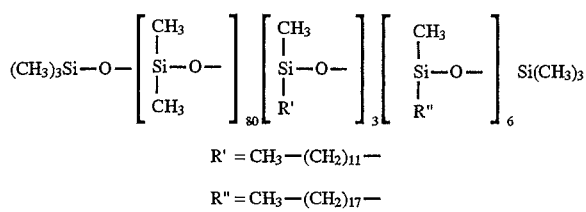

$R' = CH_3-(CH_2)_{11}-$ $R'' = CH_3-(CH_2)_{17}-$

The solubility of the alkylsiloxanes is tested to begin with by attempting to prepare solutions with 0.1 and 5% by weight of the siloxane in the respective oil. The results are summarized in Tables 1 and 2.

TABLE 1

Solubility Behavior of Different Alkylsiloxanes at a Concentration of 0.1% by weight in the Oils

| Oil | Alkylsiloxane | | | | | | |
|---|---|---|---|---|---|---|---|
| | A | B | C | D | E | F | G |
| 2-Ethylhexyl-2-ethyl hexanoate | s | s | s | s | s | s | s |
| Isopropyl myristate | s | s | s | s | s | s | s |
| Di-2-ethylhexyl adipate | s | s | s | s | s | s | s |
| Cetyl-2-ethyl hexanoate | s | s | s | s | s | s | s |
| Decyl oleate | s | s | s | s | s | s | s |
| 2-Hexyldecyl palmitate | s | s | s | s | s | s | s |
| Glycerin tricaprylate/caprate | s | s | s | s | s | s | i |
| Jojoba oil | s | s | s | s | s | s | i |
| Avocado oil | s | s | s | s | s | s | i |
| Paraffin oil (viscosity (25° C.) 38 mPas) | s | s | s | s | s | s | s |
| Paraffin oil (viscosity (25° C.) 230 mPas) | s | s | s | s | s | s | i | s = soluble
i = insoluble

TABLE 21

Solubility Behavior of Different Alkylsiloxanes at a Concentration of 5% by weight in the Oils

| Oil | Alkylsiloxane | | | | | | |
|---|---|---|---|---|---|---|---|
| | A | B | C | D | E | F | G |
| 2-Ethylhexyl-2-ethyl hexanoate | s | s | s | s | s | s | s |
| Isopropyl myristate | s | s | s | s | s | s | s |
| Di-2-ethylhexyl adipate | s | s | s | s | s | s | s |
| Cetyl-2-ethyl hexanoate | s | s | s | s | s | s | s |
| Decyl oleate | s | s | s | s | s | s | i |
| 2-Hexyldecyl palmitate | s | s | s | s | s | s | i |
| Glycerin tricaprylate/caprate | s | s | s | s | s | s | i |
| Jojoba oil | s | s | s | i | i | i | i |
| Avocado oil | s | s | s | i | i | i | i |
| Paraffin oil (viscosity (25° C.) 38 mPas) | s | s | s | s | s | s | s |
| Paraffin oil (viscosity (25° C.) 230 mPas) | s | s | s | s | s | s | i | s = soluble
i = insoluble

The spreading of the alkylsiloxanes is tested on two different materials, namely on polypropylene and on gelatin.

To prepare the gelatin layers, 1 mL of a 1% aqueous gelatin solution is distributed uniformly on a 5×5 cm² glass plate with the help of a pipette. The gelatin layer is allowed to solidify by cooling to a temperature of 0° to 5° C. The coated plates are subsequently stored for 3 days at 25° C. and 65% relative humidity.

The polypropylene sheet used is commercially available (Forco-OPPB/AT-OPAL sheet, Fa. 4P Folie Forchheim GmbH, Germany).

For determining the spreading, 10 μL of the oil or the solution are placed on a gelatin-coated glass plate or on the polypropylene sheet at a temperature of 25° C. and a relative humidity of 65%. After 10 minutes, the wetted area is measured. The results, obtained with ester oils on gelatin, are listed in Table 3. The alkylsiloxanes are used at a concentration of 0.1% by weight. The results obtained with mineral oils on polypropylene and gelatin are summarized in Tables 4 and 5. Here the alkylsiloxanes are used at a concentration of 5% by weight. The areas, over which the oil has spread, are given in mm².

TABLE 3

Spreading of Ester Oils Containing 0.1% by Weight of Alkylsiloxane on Gelatin

| Oil | Alkylsiloxane | | | | | | | |
|---|---|---|---|---|---|---|---|---|
| | None | A | B | C | D | E | F | G |
| 2-Ethylhexyl-2-ethyl hexanoate | 253 | 260 | 228 | 263 | 258 | 247 | 298 | 756 |
| Isopropyl myristate | 195 | 192 | 169 | 231 | 267 | 227 | 293 | 702 |
| Di-2-ethylhexyl adipate | 186 | 175 | 175 | 192 | 201 | 194 | 220 | 236 |
| Cetyl-2-ethyl hexanoate | 163 | 146 | 122 | 161 | 182 | 163 | 172 | 274 |
| Decyl oleate | 72 | 68 | 92 | 154 | 163 | 150 | 172 | 165 |
| 2-Hexyldecyl | 45 | 46 | 45 | 74 | 58 | 60 | 111 | 112 |

TABLE 3-continued

Spreading of Ester Oils Containing 0.1% by Weight of Alkylsiloxane on Gelatin

| Oil | Alkylsiloxane | | | | | | |
|---|---|---|---|---|---|---|---|
| | None | A | B | C | D | E | F | G |
| palmitate | | | | | | | | |
| Glycerin tri-caprylate/caprate | 96 | 88 | 101 | 158 | 153 | 163 | 165 | i |
| Jojoba oil | 50 | 57 | 65 | 95 | 95 | 60 | 102 | i |
| Avocado oil | 48 | 45 | 52 | 87 | 50 | 50 | 85 | i | i—insoluble

TABLE 4

Spreading of Mineral Oils Containing 5% by Weight of Alkylsiloxane on Polypropylene

| Oil | Alkylsiloxane | | | | | |
|---|---|---|---|---|---|---|
| | None | C | D | E | F | G |
| Paraffin oil (38 mPas) | 131 | 226 | 207 | 218 | 227 | 227 |
| Paraffin oil (230 mPas) | 64 | 104 | 108 | 95 | 101 | i | i—insoluble

TABLE 5

Spreading of Mineral Oils Containing 5% by Weight of Alkylsiloxane on Gelatin

| Oil | Alkylsiloxane | | | | | |
|---|---|---|---|---|---|---|
| | None | C | D | E | F | G |
| Paraffin oil (38 mPas) | 52 | 99 | 113 | 140 | 88 | 135 |
| Paraffin oil (230 mPas) | 31 | 82 | 57 | 86 | 77 | i | i—insoluble

It can be inferred from the Tables that, in some cases, a slight, but usually no improvement in spreading can be achieved with siloxanes A and B which are not of the invention. The spreading capability of some oils is even reduced by the addition.

On the other hand, in comparison with the pure oils, the spreading capability of all mixtures with alkylsiloxane C to G (of the invention) is clearly improved. In general, the best results are obtained with the higher molecular weight alkylsiloxanes, particularly with the alkylsiloxane G. On the other hand, however, it should be taken into consideration that the solubility of the siloxane decreases with the increasing molecular weight. In order to obtain an optimum improvement in spreading capability, it is therefore necessary to coordinate the selection of the siloxane with the respective oil in a well balanced manner. The molecular weight or the viscosity of the oil can be used as selection criteria for this purpose.

EXAMPLE 2

Water-in-Oil Emulsion, Suitable as Night Cream

Two night creams are described, which differ in the composition of the oil phase. The difference consists of the additional use of an alkylsiloxane in Formulation II. The alkylsiloxane corresponds to Formula C (see Example 1).

| Formulation (Data in %) | I | II |
|---|---|---|
| Oil phase: | | |
| Triglycerin trioleate | 4.0 | 4.0 |
| Beeswax | 1.5 | 1.5 |
| Castor wax | 1.5 | 1.5 |
| Glycerin tricaprylate/caprate | 12.5 | 12.0 |
| Avocado oil | 12.5 | 12.0 |
| Alkylsiloxane C | — | 1.0 |
| Water phase: | | |
| Magnesium sulfate heptahydrate | 0.6 | 0.6 |
| Glycerin | 2.0 | 2.0 |
| 2-Bromo-2-nitropropane-1,3-diol[1)] | 0.1 | 0.1 |
| Water | 65.3 | 65.3 |

[1)]Preservative

To prepare the cream, the aqueous phase, the temperature of which is 25° C., is introduced with vigorous stirring into the oil phase heated to 85° C. The product is subsequently homogenized with a colloid mill.

In comparison to the cream prepared according to Formulation I, the cream prepared according to Formulation II has improved application properties. It can be distributed easily and the skin acts smoother and less fatty.

EXAMPLE 3

Water-in-Oil Emulsion, Suitable as Sunscreen Cream

Two sunscreen creams are described, which differ with respect to the composition of the oil phase. The difference consists in the additional use of an alkylsiloxane in Formulation II. The alkylsiloxane corresponds to that of Formula G (see Example 1).

| Formulation (Data in %) | I | II |
|---|---|---|
| Oil phase: | | |
| Abil EM 90[1)] | 2.5 | 2.5 |
| Ceresin[2)] | 1.0 | 1.0 |
| Castor wax | 0.5 | 0.5 |
| Isohexadecane | 7.0 | 7.0 |
| Octyl methoxycinnamate | 3.0 | 3.0 |
| Octyl stearate | 13.0 | 12.75 |
| Titanium dioxide dispersion[3)] | 10.0 | 10.0 |
| Alkylsiloxane G | — | 0.25 |
| Water phase: | | |
| Sodium chloride | 0.5 | 0.5 |
| 2-Bromo-2-nitropropane-1,3-diol[4)] | 0.1 | 0.1 |
| Water | 62.4 | 62.4 |

[1)]Organosilcon emulsifier for W/O emulsion, a commercial product from Th. Goldschmidt AG
[2)]Microcrystalline hydrocarbon wax
[3)]Consisting of 30% ultrafine TiO$_2$ in octyl palmitate
[4)]Preservative The creams are prepared according to the directions of Example 2.

The sun-screening effect of Formulations I and II was investigated in vivo on people, following the directions of DIN 67 501. An SPF (sun protection factor) of 8.9 was obtained for Formulation I and of 13.7 for Formulation II. The results confirm the superior effectiveness of Formulation II which, because of the addition of the alkylsiloxane G, contains an oil phase with improved spreading action.

EXAMPLE 4

Oil-in-Water Emulsion, Suitable as Sunscreen Cream

Two sunscreen creams are described which differ with respect to the composition of the oil phase. The difference consists in the additional use of an alkylsiloxane in Formulation II. The alkylsiloxane corresponds to that of Formula G (see Example 1).

| Formulation (Data in %) | I | II |
|---|---|---|
| Oil phase: | | |
| TEGO Care 450[1] | 2.0 | 2.0 |
| Octyl palmitate | 6.5 | 6.5 |
| Paraffin oil[2] | 6.5 | 6.0 |
| Octyl methoxycinnamate | 4.0 | 4.0 |
| 2-Hydroxy-4-methoxybenzophenone | 1.0 | 1.0 |
| Alkylsiloxane G | — | 0.5 |
| Water phase: | | |
| Glycerin | 3.0 | 3.0 |
| Carbopol 941[3] | 20.0 | 20.0 |
| 2-Bromo-2-nitropropane-1,3-diol[4] | 0.1 | 0.1 |
| Water | 56.9 | 56.9 |

[1] Triglycerin stearate/methylglucose stearate, emulsifier for O/W emulsions, commercial product of Th. Goldschmidt AG
[2] Viscosity of 30 mpas
[3] Thickener, commercial product of the Goodrich Company
[4] Preservative To prepare the creams, the oil and water phases are heated to 70° to 75° C., added together at this temperature and homogenized using a rotor-stator stirrer until the droplets have size of 3 to 5 μm. Subsequently, the temperature is reduced to 30° C. while stirring slowly.

The sun-screening effect of Formulations I and II was investigated in vivo on people, following the directions of DIN 67 501. An SPF (sun protection factor) of 5.2 was obtained for Formulation I and of 7.0 for Formulation II. The results confirm the superior effectiveness of Formulation II which, because of the addition of the alkylsiloxane G, contains an oil phase with improved spreading action.

EXAMPLE 5

Oil-in-Water Emulsion, Suitable as Day Cream

Two formulations are described, which differ with respect to the composition of the oil phase. The difference consists in the additional use of an alkylsiloxane in Formulation II. The alkylsiloxane corresponds to that of Formula F (see Example 1).

| Formulation (Data in %) | I | II |
|---|---|---|
| Oil phase: | | |
| TEGIN[1] | 6.0 | 6.0 |
| Stearic acid | 2.0 | 2.0 |
| Octyl palmitate | 7.0 | 7.0 |
| Hexadecyl palmitate | 10.0 | 8.5 |
| Alkylsiloxane F | — | 1.5 |
| Water phase: | | |
| Glycerin | 1.9 | 1.9 |
| 2-Bromo-2-nitropropane-1,3-diol[2] | 0.1 | 0.1 |
| Water | 75.0 | 75.0 |

[1] Self-emulsifying glycerin monostearate/distearate, a commercial product of Th. Goldschmidt AG
[2] Preservative To prepare the creams, the oil phase and the water phase are heated to 65° to 70° C. and added together at this temperature. Subsequently, the procedure is identical with that of Example 4.

In comparison to the cream prepared using Formulation I, the cream prepared using Formulation II has improved application properties. It can be distributed easily, the skin is more supple and less dull.

EXAMPLE 6

Oil-in-Water, Suitable as Body Lotion

Two formulations are described, which differ with respect to the composition of the oil phase. The difference consists in the additional use of an alkylsiloxane in Formulation II. The alkylsiloxane corresponds to that of Formula G (see Example 1).

| Formulation (Data in %) | I | II |
|---|---|---|
| Oil phase: | | |
| PEG-15 stearyl alcohol | 1.5 | 1.5 |
| Glycerin mono/distearate | 1.0 | 1.0 |
| Stearyl alcohol | 2.0 | 2.0 |
| Octyl palmitate | 5.5 | 5.0 |
| Paraffin oil[1] | 5.0 | 5.0 |
| Alkylsiloxane G | — | 0.5 |
| Water phase: | | |
| Glycerin | 2.9 | 2.9 |
| 2-Bromo-2-nitropropane-1,3-diol[2] | 0.1 | 0.1 |
| Water | 82.0 | 82.0 |

[1] Self-emulsifying glycerin monostearate/distearate, commercial product of Th. Goldschmidt AG
[2] Preservative To prepare the creams, the oil phase and the water phase are heated to 75° to 80° C. and added together at this temperature. Subsequently, the procedure is identical with that of Example 4.

In comparison to the cream prepared according to Formulation I, the cream prepared according to Formulation II has improved application properties. It can easily be dispersed, the development of white areas during the dispersal is prevented and the skin is more supple and less wax-like dull.

We claim:

1. Cosmetic or pharmaceutical preparation containing oils selected from the group consisting of of ester oils, animal oils, vegetable oils, mineral oils and fats and exhibiting an improved spreading behavior, comprising organopolysiloxane of the formula

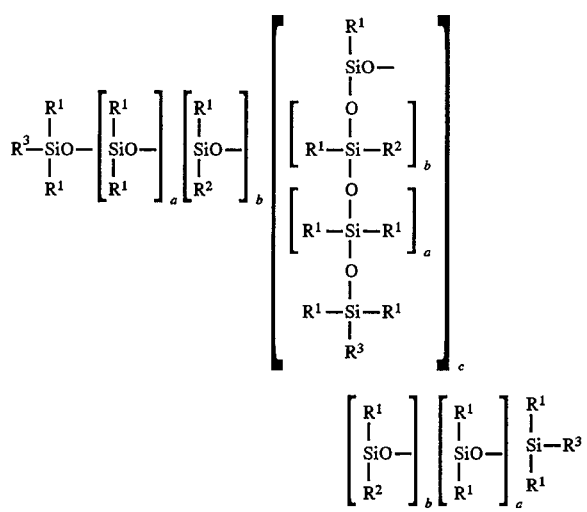

wherein $R^1$ is the same or different and represents alkyl groups with 1 to 4 carbon atoms, with the proviso that at least 90% of the $R^1$ groups are methyl groups, $R^2$ is the same or different and
(1) can be linear or branched alkyl groups 8 to 30 carbon atoms, wherein the alkyl groups can be interrupted by an oxygen atom, or
(2) can be linear or branched alkoxy groups with 8 to 30 carbon atoms, wherein the alkyl group of the alkoxy groups can be interrupted by an oxygen atom, $R^3$ represents the $R^1$ or the $R^2$ group, a has a value of 5 to 80, b as a value of 0 to 20, and c has a value of 0 to 5, in an amount of about between 0.003 and 20% by weight based on the total weight of oil and organopolysiloxane with the proviso that (i) in an average molecule at least two $R^2$ groups are present and are as defined in (1), (2), or both above, (ii) a>b and the sum of the units with the subscript a>10, and (iii) the organopolysiloxane is homogeneously miscible with the oil in a concentration of 0.01 to 20% by weight.

2. The preparation of claim 1, wherein the subscript c has a value of 0.

3. The preparation according to claim 1 or 2, where in the organopolysiloxane is selected from the group consisting of (i) molecular weight>500, the sum of the units with the subscript a=12 to 35, the sum of the units with the subscript b=3 to 10, and the subscript c=0, (ii) molecular weight>400 and molecular weight <500, the sum of the units with the subscript a=25 to 60, the sum of the units with the subscript b=5 to 15, and the subscript c=0, and (iii) molecular weight<400, the sum of the units with the subscript a=45 to 80, the sum of the units with the subscript b=3 to 20, and the subscript c=0.

4. The preparation according to claim 1 or 2, wherein the oil is mineral oil is having viscosity at 25° C. and the organopolysiloxanes is selected from the group consisting of (i) viscosity>50 mpas, the sum of the units with the subscript a=12 to 60, the sum of the units with the subscript b=3 to 15, and the subscript c=0, and (ii) viscosity<50 mpas, the sum of the units with the subscript a=26 to 80, the sum of the units with the subscript b=3 to 20, and the subscript c=0.

* * * * *